United States Patent [19]

Breborowicz et al.

[11] Patent Number: 5,597,805
[45] Date of Patent: Jan. 28, 1997

[54] PERITONEAL DIALYSIS SOLUTIONS

[75] Inventors: Andrzej Breborowicz, Posnan, Poland; Dimitrios G. Oreopoulos, Etobicoke, Canada

[73] Assignee: Baxter International Inc., Deerfield, Ill.

[21] Appl. No.: 77,815

[22] Filed: Jun. 15, 1993

Related U.S. Application Data

[63] Continuation of Ser. No. 830,721, Feb. 4, 1992, abandoned.

[51] Int. Cl.$^6$ .................................................. A61K 38/00
[52] U.S. Cl. ................................................ 514/19; 514/23
[58] Field of Search ................................. 514/19, 23, 59

[56] References Cited

U.S. PATENT DOCUMENTS

| | | | |
|---|---|---|---|
| 4,339,433 | 7/1982 | Kartinos et al. | 424/78 |
| 4,574,085 | 3/1986 | Dolkart et al. | 424/148 |
| 4,761,237 | 8/1988 | Alexander et al. | 210/647 |
| 4,828,561 | 5/1989 | Woodruff | 623/3 |
| 4,863,907 | 9/1989 | Sakurai et al. | 514/56 |
| 4,880,629 | 11/1989 | Okamoto et al. | 424/658 |
| 4,886,789 | 12/1989 | Milner | 514/60 |
| 4,906,616 | 3/1990 | Gilchrist et al. | 514/21 |
| 4,959,175 | 9/1990 | Yatzidis | 252/364 |
| 4,976,683 | 12/1990 | Gauthier et al. | 609/29 |
| 5,011,826 | 4/1991 | Steudle et al. | 514/23 |
| 5,039,609 | 8/1991 | Klein . | |

FOREIGN PATENT DOCUMENTS

| | | |
|---|---|---|
| 1239586 | 7/1988 | Canada . |
| 2196724 | 8/1990 | Japan . |

OTHER PUBLICATIONS

Morrison et al, Organic Chemistry, 3rd edition, (1979) pp. 1132–1143.

"Effects of Chondroitin Sulphate on Fluid and Solute Transport During Peritoneal Dialysis in Rats"; Breborowicz et al., Peritoneal Dialysis International, ol. 11, pp. 351–354; 1991.

"Cytotoxic Effects of Commercial Continuous Ambulatory Peritoneal Dialysis (CAPD) Fluids of Bacterial Exoproducts on Human Mesothelial Cells In Vitro"; Bronswijk et al., Peritoneal Dialysis Intl., vol. 9, pp. 197–202, 1969.

Abstracts 17, 18, 19 and 20, *Peritoneal Dialysis International*, vol. 10 (1990) published Feb. 8, 1990.

Abstracts 30–35, *Peritoneal Dialysis International*, vol. 11 (1991), published Feb. 6, 1991.

*Primary Examiner*—Elli Peselev
*Attorney, Agent, or Firm*—Thomas S. Borecki; Charles R. Mattenson; Robert M. Barrett

[57] ABSTRACT

Peritoneal dialysis solutions are specially formulated for use during and immediately after an episode of peritonitis. The solutions include one or more additives to minimize the injury and physiological effects that peritonitis can cause. One additive is a mixture of amino acids sufficient to maintain a positive nitrogen balance, at least one of the amino acids being present in a dipeptide form. Another additive is a compound that scavenges free radicals generated by peritoneal macrophages activated by the peritonitis. Another additive is chondroitin sulfate that changes the permeability of the peritoneal membrane during subsequent dialysis using solutions free of chondroitin sulfate. Another additive is the degradation products of hyaluronic acid to enhance the regeneration of the peritoneal mesothelium without fibrosis.

2 Claims, 2 Drawing Sheets

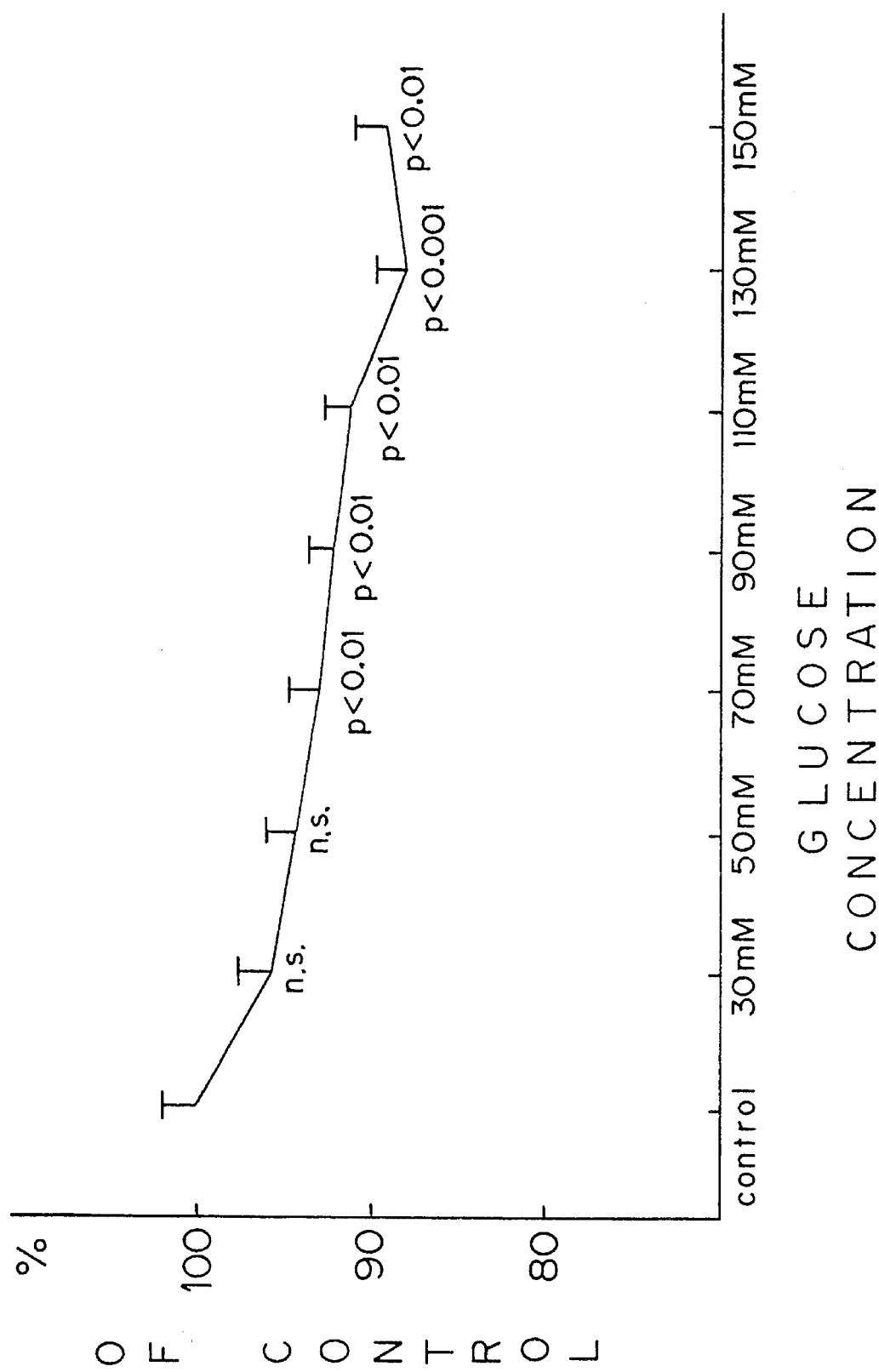

PERITONEAL DIALYSIS SOLUTIONS

This is a continuation of application Ser. No. 07/830,721 filed on Feb. 4, 1992, now abandoned.

FIELD OF THE INVENTION

The invention generally relates to peritoneal dialysis solutions, especially those used in the practice of continuous ambulatory peritoneal dialysis, or CAPD.

BACKGROUND OF THE INVENTION

Peritoneal dialysis periodically infuses sterile aqueous solution into the peritoneal cavity. Diffusion exchange takes place between the solution and the bloodstream across the natural body membranes. The diffusion removes the waste products that the kidneys normally excrete. The waste products typically consist of solutes like sodium and chloride ions, and the other compounds normally excreted through the kidneys like as urea, creatinine, and water. The diffusion of water across the peritoneal membrane during dialysis is called ultrafiltration.

The inflammation of the peritoneum, called peritonitis, is an undesired complication of peritoneal dialysis. The inflammation may lead to loss of mesothelial cells and the excessive growth of fibrous connective tissue in the peritoneum membrane, called fibrosis. These reactions can lead to the loss of ultrafiltration during dialysis.

In addition, peritonitis may lead to increased protein loss in the patient, with the patient not feeling well enough to eat to replace this loss.

To make up for the reduction in normal ultrafiltration rates, peritoneal dialysis patients experiencing peritonitis often receive hypertonic dialysis solutions, typically containing glucose as an osmotic solute. However, the use of hypertonic solutions for these purposes may be counterproductive. Due to their low pH, high osmolarity, and the presence of glucose, the solutions may inhibit the necessary regeneration of mesothelial cells. They also may lead to the growth of fibroblasts, causing fibrosis.

To enhance the patient's anabolic state and replace protein loss experienced during peritonitis, conventional dialysis solutions also may include mixtures of nutritionally essential amino acids (like methionine, tryptophan, and isoleucine) and nutritionally non-essential amino acids (like glycine and alanine). However, the presence of these amino acids may be counterproductive, too. Many of these amino acids can inhibit the proliferation of mesothelial cells.

Therefore, there is a need for peritoneal dialysis solutions that can be used during and immediately after peritonitis without potentially counterproductive effects. The solutions would promote the replacement of mesothelial cells, minimize the formation of fibroblasts, and counter the attendant loss of ultrafiltration that peritonitis often causes.

SUMMARY OF THE INVENTION

The invention provides improved peritoneal dialysis solutions that can be used during and after episodes of peritonitis to protect the patient against the inflammatory reactions of peritonitis, fibrosis, and the loss of ultrafiltration. The invention also provides improved peritoneal dialysis solutions that can be used after episodes of peritonitis to at least partially restore ultrafiltration characteristics lost due to peritonitis.

One aspect of the invention provides peritoneal dialysis solutions that maintain a positive nitrogen balance during peritonitis without significantly inhibiting the proliferation of mesothelial cells. This aspect of the invention replaces at least some individual amino acids in the dialysis solution with amino acids in their dipeptide form.

The inventors have discovered that certain amino acids stunt the proliferation of mesothelial cells. By using these amino acids in their dipeptide form instead, significant improvements in the proliferation of mesothelial cells occur. In a preferred embodiment, at least some amino acids like methionine, tryptophan, or isoleucine appear in their dipeptide form (for example, glycine-tryptophan) to achieve this beneficial effect.

The inclusion in a peritoneal dialysis solution of amino acids in dipeptide form with other essential and non-essential amino acids enhances the anabolic state of the patient suffering peritonitis. In addition, the solution does not unduly inhibit the regeneration of mesothelial cells that is necessary to the patient's healing process.

Another aspect of the invention supplements peritoneal dialysis solution with compounds that act as scavengers of free radicals present within the peritoneal cavity. The inventors have discovered that the free radicals released by peritoneal cells during peritonitis can injure mesothelial and endothelial cells and may otherwise case disfunction of the peritoneal membrane. The presence in a peritoneal dialysis solution of compounds that scavenge these free radicals decreases the injury that the peritoneum might otherwise suffer during peritonitis. In a preferred embodiment, the scavengers are vitamin E, procysteine, superoxide dismutase, or chondroitin sulfate.

The inventors have also discovered that use of a dialysis solution containing chondroitin sulfate also beneficially changes the permeability of the peritoneal membrane during subsequent dialysis using conventional solutions. Chondroitin sulfate enhances the subsequent ultrafiltration characteristics of the peritoneal membrane using conventional dialysis solution. It also decreases the absorption of glucose and transperitoneal loss of proteins with no change in urea diffusion. Chondroitin sulfate therefore serves not only as a free radical scavenger to minimize cellular injury caused by inflammation during peritonitis, but it can be used after an episode of peritonitis to at least partially restore loss of ultrafiltration characteristics caused by peritonitis.

Another aspect of the invention includes the degradation products of hyaluronic acid as an additive to a peritoneal dialysis solution to enhance the regeneration of the peritoneal mesothelium without fibrosis. The inventors believe that these degradation products, principally oligosaccharides, will increase the proliferation of endothelial cells without affecting fibroblasts growth.

Used alone or in combination, these additive compounds make possible the formulation of peritoneal dialysis solutions specifically tailored for use during and immediately after the development of peritonitis.

These additive compounds, used alone or in combination in peritoneal dialysis solutions, can enhance the regeneration of mesothelial cells and prevent the growth of fibroblasts. They can improve the nutritional status of the patient during peritonitis. They can actively decrease the degree of damage occurring during inflammation of the peritoneal membrane. They can restore the peritoneal membrane to its pre-peritonitis condition.

The many features and the advantages of the invention will become even more apparent after reading the following detailed description, associated drawings, and claims.

BRIEF DESCRIPTION OF THE DRAWINGS

FIG. 2 is a graph showing the accumulation of $^{86}$Rb during 72 hours in HMC exposed to different high glucose concentrations, expressed as a % of control where the HMC were cultured in normotonic medium.

DESCRIPTION OF THE PREFERRED EMBODIMENTS

Figure 1:
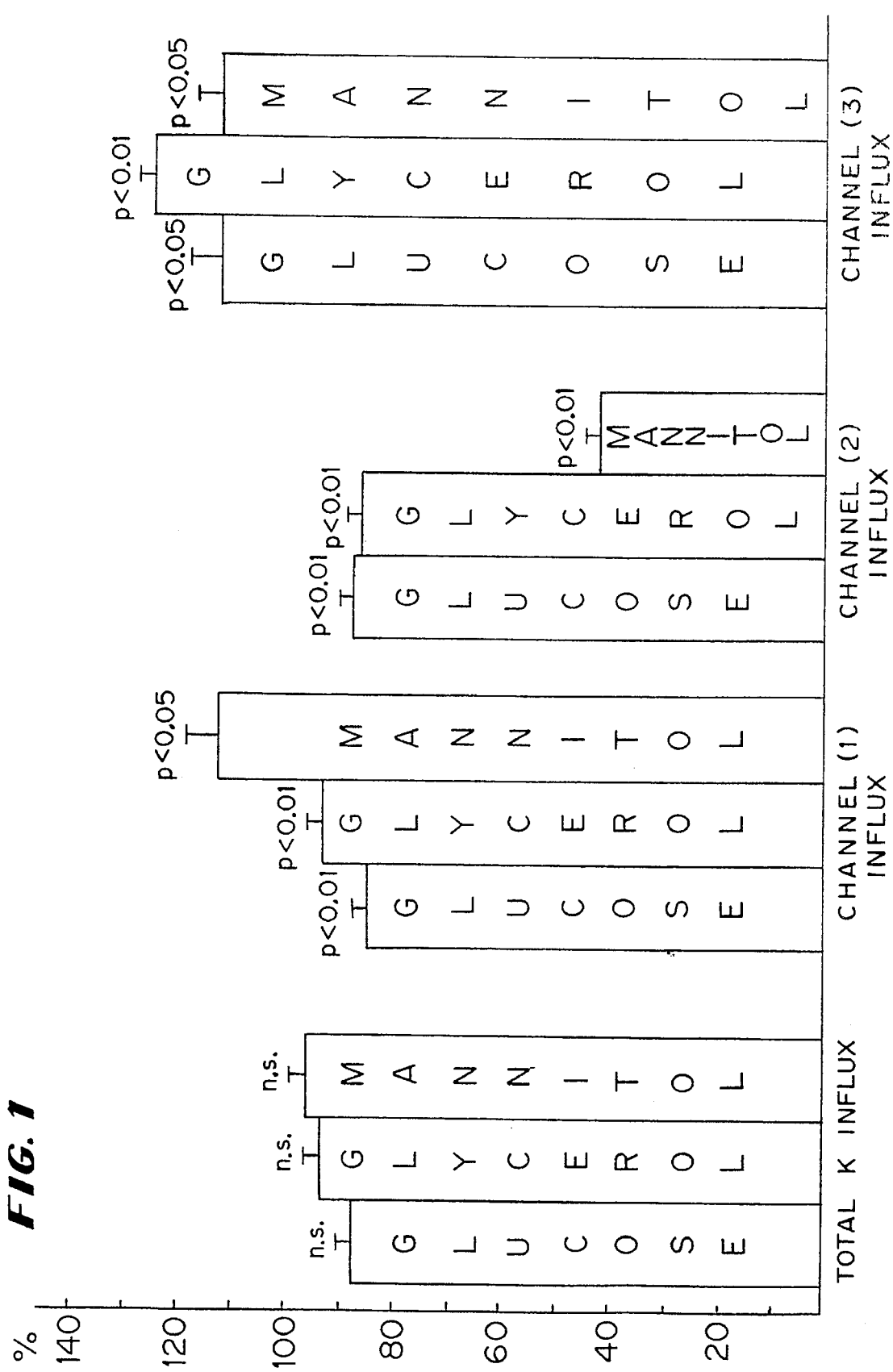
FIG. 1 is a chart showing the mean value in $^{86}$Rb uptake by human mesothelial cells (HMC) through different pathways after being cultured for 7 days in medium with high concentrations (90 mM) of glucose, glycerol, and mannitol, expressed as a % of control where the HMC were cultured in normotonic medium.

After an episode of peritonitis, the CAPD patient typically receives a hypertonic peritoneal dialysis solution containing glucose. The intent is to counteract the loss of ultrafiltration that frequently occurs during peritonitis.

However, hypertonic peritoneal dialysis solutions with glucose may actually interfere with the regeneration of mesothelial cells and thereby interfere with the patient's recovery from the inflammatory effects of peritonitis. Such solutions also may encourage the growth fibroblasts and could contribute to peritoneal fibrosis.

The inventors have experimentally determined that potassium (measured with its analog $^{86}$Rb) enters human mesothelial cells (HMC) through three different pathways:

(1) through an active channel that the glucoside ouabain blocks in a dose dependent way, which corresponds to the activity of the Na-K-ATPase pump in plasmalemma;

(2) through another active channel that the diuretic drug furosemide blocks in a dose dependent way, but that is not blocked by ouabain; and (3) through a passive channel that neither ouabain or furosemide block.

The inventors have also experimentally determined that about 60% of $^{86}$Rb transport occurs through active Channel (1), the Na-K-ATPase pump; about 29% through active Channel (2); and about 11% through passive Channel (3).

As the following Example demonstrates, exposure of HMC to hyperosmolal medium modifies the transport of $^{86}$Rb into the cells through all three pathways.

EXAMPLE 1

This study evaluated the mechanisms regulating transport of potassium from the extracellular space into HMC in in vitro culture.

HMC were isolated from omentum following the method described in Van Bronswwijk et al., "Cytotoxic Effects of Commercial Continuous Ambulatory Peritoneal Dialysis (CAPD) Fluids and of Bacterial Exoproducts on Human Mesothelial Cells in Vitro," Perit Dial Intern, 1989 (9): 197–202.

The HMC were seeded into 75 cm$^2$ culture flasks and grown to confluency. Then, the HMC were harvested with trypsin-EDTA solution and seeded into 96-well culture plates and there again grown to confluency. The study used the confluent mesothelial monolayers cultured in the 96-well plates.

HMC were incubated in the culture medium for 7 days with various osmotic solutions (90 mM and more of glucose or glycerol or mannitol). After incubation, potassium analog $^{86}$Rb was added to the medium. The uptake of $^{86}$Rb by HMC was measured and compared with the uptake in control HMC not exposed to osmotic solutes (the control HMC having been cultured in a normotonic medium).

As FIG. 1 shows, transport through the passive Channel (3) increases in HMC exposed chronically (over 7 days) to high concentration of all the osmotic solutes (90 mM). Mannitol also stimulated active transport through Channel (1), but glucose and glycerol both decreased Channel (1) transport. All solutes decreased active transport through Channel (2) as well.

As FIG. 2 shows, the intracellular accumulation of $^{86}$Rb in HMC exposed for 72 hours to increased concentrations of glucose diminished proportionally to the glucose concentration, compared to the accumulation in the control HMC.

The study demonstrates that chronic exposure of HMC to high glucose concentration (90 mM) decreases the activity of the Na-K-ATPase pump (i.e., Channel (1)), which is the main pump responsible for intracellular potassium accumulation. The activity of Channel (2) also decreases as a result to exposure of HMC to high glucose concentration.

In effect, this decreased capacity of HMC to take up potassium results in diminished accumulation of potassium in HMC. This may, in turn, cause cellular disfunction like those associated with diabetic disorders resulting from reduced Na-K-ATPase activity. See Greene et al, "Sorbitol, Phosphoinodsitides and Sodium - Potassium - ATPase in the Pathogenesis of Diabetic Complications," N Engl J Med 1987; 316: 599–606; and Yorek et al, "The Effect of Increased Glucose Levels on Na-K Pump Activity in Cultured Neuroblastoma Cells," J Neurochem 1988; 51:605–610. HMC potassium depletion also may produce severe metabolic abnormalities such as deranged protein synthesis. See Lubin, "Intracellular Potassium and Control of Protein Synthesis," Fed Proc 1964; 23: 994–997.

High concentration of glycerol, but not mannitol, produces the same effect as glucose. This suggests that the decrease in Na-K-ATPase pump activity depends upon the metabolism of the osmotic solute inside the cell, since both mannitol influx and metabolism in HMC are probably small.

The study also shows that chronic exposure of HMC to all osmotic solutes increases the passive permeability (via Channel (3)) of the plasmalemma to $^{86}$Rb. This may be due to a "washout" of structural components of the plasmalemma, causing increased leakage and loss of intracellular metabolic substrates. This, too, can lead to cellular disfunction.

Thus, increased extracellular tonicity due to high glucose concentration may cause HMC potassium loss both through diminished active influx, mostly by reduced Na-K-ATPase activity, and through an outflux of ion-rich water ("washout") from the cells due to a negative osmotic gradient. Also see Moreno et al., "Increase in Serum Potassium Resulting from the Administration of Hypertonic Mannitol and Other Solutions," J Lab Clin Med 1969; 73: 291–294.

The presence of these disfunctions does not promote the regeneration of mesothelial cells necessary to the healing process during and after a peritonitis episode.

The peritoneal dialysis solutions that embody the features of the invention are specially formulated for patients for use during and immediately after episodes of peritonitis. The solutions promote the healing process to avoid or at least minimize the injury and adverse physiological effects of peritonitis upon the dialysis regime of the patient.

Like conventional peritoneal dialysis solutions, the solutions that embody the features of the invention include:

(1) physiological salts such as sodium chloride, calcium chloride and sodium acetate in appropriate concentrations to maintain a normal electrolyte profile. Typical concentrations are from 116 to 140 mEq/liter of sodium; 0 to 6 mEq/liter of calcium, and 100 to 144 mEq/liter of chloride.

(2) lactate or bicarbonate in appropriate concentrations to maintain a physiologically tolerable pH of between about 5 to about 7.4. Typical concentrations are from 30 to 45 mEq/liter of lactate; and (3) glycerol or glucose polymers at a concentration (at least 0.5 percent by weight) sufficient to generate the necessary osmotic pressure to remove water from the patient through ultrafiltration.

According to the invention, the solutions contain one or more of the following additives:

(4) a mixture of essential and non-essential amino acids to serve as a source of supplemental nitrogen for the support of protein synthesis for the patient and to counterbalance the protein that the patient loses because of peritonitis. According to this aspect of the invention, at least some of these amino acids are present in their dipeptide form to promote the proliferation of mesothelial cells lost during peritonitis.

(5) a compound that scavenges free radicals produced by peritoneal cells that causes peroxidation of the peritoneum;

(6) chondroitin sulphate to restore at least a portion of transperitoneal transport lost due to peritonitis;

(7) compounds consisting of the degradation products of hyaluronic acid to enhance the regeneration of the peritoneal mesothelium without fibrosis.

The following sections describe the benefits associated with each Additive (4) to (7).

AMINO ACID ADDITIVE (4)

A preferred embodiment of the amino acid additive (4) comprises, based on one liter of solution, about 0.1 to 10 mM each of the nutritionally essential amino acids methionine, tryptophan, isoleucine, valine, leucine, lysine, histidine, threonine, and phenylalanine, at least some of which are present in their dipeptide form. When present as dipeptides, these amino acids do not inhibit mesothelial cell proliferation as much as they do when present as individual amino acids.

The most preferred embodiment includes at least tryptophan in its dipeptide form (glycine-tryptophan, or gly-trp), as the individual amino acid tryptophan inhibits mesothelial cell proliferation more than an other individual amino acid.

The mixture also includes about 0.1 to 10 mM each of arginine, alanine, proline, glycine, serine, tyrosine, cysteine (cystine), and other individual, nutritionally non-essential amino acids as required to maintain a positive nitrogen balance in the patient.

The following Example illustrates the benefits of using amino acids in a dialysis solution, of which certain are in their dipeptide form.

EXAMPLE 2

This study evaluated the toxicity of a mixture of essential and non-essential amino acids on the proliferation of HMC in conditions simulating peritoneal dialysis.

HMC prepared as described in Example 1 were exposed to essential and nonessential amino acids. Adverse effects were measured in terms of the impact upon cell proliferation (as measured by incorporation of 3H-thymidine) and the release of LDH from cell cytoplasm.

All the amino acids evaluated inhibited the proliferation of HMC when present. Tryptophan exhibited the most inhibition effect.

When HMC are exposed to tryptophan in a concentration of 5 mM for 24 hours, their proliferation is reduced by 82% compared to the proliferation of control HMC cells not exposed to tryptophan. After 24 hours of exposure, tryptophan (5 mM) also increased the leakage of LDH from the mesothelial monolayer HMC by 740%, compared to the control HMC cells.

In contrast, after 24 hours of exposure to dipeptide tryptophan (gly-trp) in concentration of 5 mM, proliferation of HMC decreased by only 30% and LDH release increased by only 180%, compared to the control HMC cells.

In another experiment, growing HMC were exposed to two mixtures each having a high concentration of amino acids (1.1%). One amino acid mixture contained tryptophan. The other amino acid mixture contained gly-trp instead of tryptophan. The concentration of both amino acid mixtures was progressively decreased by dilution down to 0.22% in 6 hours. The HMC were incubated for 18 additional hours in media with the low (0.22%) concentration.

The mixture of amino acids containing tryptophan reduced 3H-thymidine incorporation by 30%, compared to the control HMC not exposed to any amino acid mixture. The mixture of amino acids in which the gly-trp replaced the tryptophan reduced 3H-thymidine incorporation by only 17%. The inclusion of the dipeptide form of the amino acid in the mixture reduced the undesired effect by about 50%.

FREE RADICALS SCAVENGER ADDITIVE (5)

Peritonitis activates peritoneal macrophages (as proved by others). The activation of the macrophages leads to the increased generation of free radicals. The inventors believe that the increased generation of free radicals causes peritoneal peroxidation.

According to this aspect of the invention, the use of compounds that scavenge free radicals in peritoneal dialysis solutions minimizes or alleviates peritoneal peroxidation during episodes of peritonitis.

The inventors have also shown that the increased presence of free radicals also injures mesothelial cells in the peritoneum. The free radicals probably also injure endothelial cells, too. The free radicals can depolymerize hyaluronic acid and/or collagen in interstitium, causing disfunction of the peritoneal membrane.

According to this aspect of the invention, these undesired effects of peritonitis also can be minimized or lessened by supplementing the dialysis solution with free radical scavengers.

EXAMPLE 3

In one experiment, exposure to normal saline in the peritoneal cavities of rats for over 6 days increased peroxidation of the peritoneal membrane, as measured by the concentration of malondialdehyde in the animal's omentum: 8.12+/−0.51 uM/100 ug tissue (n=7) in controls not infused with saline, compared to 11.36+/−1.07 uM/100 ug tissue (n=12) in rats infused with saline. In another experiment, one group of rats (n=22) was infused over 6 days with saline supplemented with vitamin E (0.1 g %). Another control group of rats (n=18) was infused over 6 days with saline alone. In rats infused with the vitamin E-supplemented saline, the concentration of malondialdehyde in the omentum (and therefore the severity of peritoneal peroxidation) was lower (4.53+/−0.30 uM/100 ug tissue) than in the rats infused with saline alone (9.38+/−0.90 uM/100 ug tissue).

In other in vitro experiments, free radicals generated by an xanthine-xanthine oxidase system were observed to injure mesothelial cells. The injury was prevented by using vitamin E (0.1% to 1.0%) and chondroitin sulphate (0.1%).

In another experiment, the xanthine-xanthine oxidase system was added to dialysis solution (2.5% dextrose). The solution was infused into the peritoneal cavities of rats. The increased presence of the free radicals generated by the infused oxidase system caused loss of ultrafiltration and increased glucose absorption, the same physiological effects observed during episodes of peritonitis. This result further links the increased presence of free radicals to the inflammatory effects and injury of peritonitis.

The addition of free radical scavenger vitamin E (0.01%) reduced or totally reversed the adverse effects caused by the free radicals generated by the xanthine-xanthine oxidase system. The free radical scavenger would have the same beneficial effect in the increased presence of the free radicals during peritonitis.

In a preferred embodiment, the scavengers are selected from the group consisting of vitamin E, procysteine, superoxide dismutase, and chondroitin sulfate and are present in concentrations of about 0.01 to 0.5 g %.

TRANSPORT RESTORATION ADDITIVE (6)

Peritonitis can adversely alter peritoneal transport, leading to a reduction of ultrafiltration. According to this aspect of the invention, the peritoneal dialysis solution includes chondroitin sulphate to change or restore transperitoneal transport after an episode of peritonitis.

EXAMPLE 4

Saline supplemented with chondroitin sulphate (0.1 g %) was infused into the peritoneal cavity of rats over a period of six days. Then, conventional 2.5% Dianeal peritoneal dialysis solution (sold by Baxter Healthcare Corporation, Deerfield, Ill.) was infused into the peritoneal cavities of the rats.

The chronic exposure to the chondroitin sulphate modified the permeability of the peritoneal membrane during the subsequent dialysis with conventional dialysis solution. The net ultrafiltration measured after a dwell period of four hours was more than the ultrafiltration measured before exposure to the chondroitin sulphate. Also, absorption of glucose from the dialysate and transperitoneal loss of proteins decreased, with no change in urea diffusion, when compared to these same transport parameters measured before chronic exposure to the chondroitin sulphate.

This Example illustrates the benefits of using chondroitin sulphate in a dialysis solution to restore transperitoneal transport after an episode of peritonitis.

In a preferred embodiment, the chondroitin sulphate is present in a concentration of about 0.01 to 0.5 g %.

REGENERATION ADDITIVE (7)

Wound healing during fetal life is characterized by healing without fibrosis or scar formation. It is believed that this healing process is at least partly mediated by the high concentration of hyaluronic acid in a fetal wound extramural matrix. By increasing the concentrations of hyaluronic acid in the extracellular fluids of adults, the healing of wounds without fibrosis is enhanced.

Other studies have shown that the hyaluronic acid is not responsible by itself. It is believed that its degradation products (oligosaccharides) that are the active agents in promoting fibrosis-free wound healing. In in vitro experiments, oligosaccharides products of the degradation of hyaluronic acid increase the proliferation of endothelial cells without effect on fibroblasts growth.

According to this aspect of the invention, peritoneal dialysis solution includes degradation products of hyaluronic acid to enhance the regeneration of the peritoneal mesothelium without fibrosis.

The dialysis solutions containing one or more of the additives (4) to (7), when sterile, may be used as the peritoneal dialysis solution in a conventional CAPD procedure, using the techniques and equipment developed and sold by the Baxter Healthcare Corporation, Deerfield, Ill.

The above description and Examples are for illustrative purposes only. They are not intended to limit the scope of the inventions, as defined in the following claims.

We claim:

1. A peritoneal dialysis solution comprising:

physiological salts in concentrations sufficient to affect the removal of solutes by diffusion from the patient's blood across the peritoneal membrane into the solute, and a mixture of amino acids sufficient to contribute to protein synthesis and a positive nitrogen balance, wherein tryptophan is present in a glycine-tryptophan form, the glycine-tryptophan present in a concentration of about 2 mM to about 10 mM based upon one liter of solution, to aid the proliferation of mesothelial cells.

2. A solution according to claim 1 and further including an osmotic solute selected from the group consisting of glucose and glycerol in concentrations sufficient to create an osmotic pressure to effect the removal of water by diffusion from the patient's blood across the peritoneal membrane into the solution.

* * * * *